(12) United States Patent
Iwai et al.

(10) Patent No.: US 8,722,931 B2
(45) Date of Patent: May 13, 2014

(54) COMPOUND AND METHOD FOR PREPARING THE SAME

(75) Inventors: Yu Iwai, Shizuoka (JP); Takafumi Nakayama, Shizuoka (JP); Junya Abe, Shizuoka (JP); Ichiro Koyama, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 182 days.

(21) Appl. No.: 13/333,500

(22) Filed: Dec. 21, 2011

(65) Prior Publication Data

US 2012/0165572 A1 Jun. 28, 2012

(30) Foreign Application Priority Data

Dec. 22, 2010 (JP) ................................. 2010-286765
Nov. 18, 2011 (JP) ................................. 2011-253229

(51) Int. Cl.
*C07C 233/38* (2006.01)

(52) U.S. Cl.
USPC ............ 564/204; 564/144; 564/207; 564/208

(58) Field of Classification Search
USPC .................................. 564/144, 204, 207, 208
See application file for complete search history.

(56) References Cited

U.S. PATENT DOCUMENTS 4,009,256 A 2/1977 Nowak, Jr. et al.
5,696,193 A * 12/1997 Daniel et al. .................. 524/408

FOREIGN PATENT DOCUMENTS

JP 50-89407 A 7/1975
JP 61-68456 A 4/1986

OTHER PUBLICATIONS

Zhicheng Deng et al., "Facile Synthesis of Controlled-Structure Primary Amine-Based Methacrylamide Polymers via the Reversible Addition-Fragmentation Chain Transfer Process", Journal of Polymer Science, Part A Polymer Chemistry, vol. 46, 2008, pp. 4984-4996.
Extended European Search Report for European Application No. 11195183.6 dated Mar. 30, 2012.

* cited by examiner

*Primary Examiner* — Shailendra Kumar

(74) *Attorney, Agent, or Firm* — Birch, Stewart, Kolasch & Birch, LLP

(57) ABSTRACT

The invention is directed to a compound represented by the Formula (1) as defined herein, and a method for preparing a compound represented by the Formula (1) which includes: reacting a diamine compound represented by the Formula (2) as defined herein with a methacrylic anhydride or an acrylic anhydride under a condition where an organic acid having a pKa of 2.0 or more is present in an amount of 0.5 to 5.0 moles based on 1 mole of the diamine compound to obtain a reaction mixture; adding phosphoric acid to the reaction mixture; and purifying the reaction mixture by extraction with an organic solvent.

8 Claims, No Drawings

COMPOUND AND METHOD FOR PREPARING THE SAME

FIELD OF THE INVENTION

The present invention relates to a novel compound and a method for preparing the same. Specifically, the present invention relates to a novel radical polymerizable compound as a salt of a (meth)acrylamide having a primary amine structure, and a method for preparing the same. The compound of the present invention and a polymerizate thereof are used in various applications, including polymeric surfactants, shampoo compositions, hydrophilic members and coating materials.

BACKGROUND OF THE INVENTION

Radical polymerizable monomers having a primary amine structure and polymerizates thereof are currently used in biomedical applications (such as drugs and gene carriers), polymeric surfactants, shampoo compositions, hydrophilic members and coating materials and other applications. However, such radical polymerizable monomers are very difficult to synthesize and have poor storage stability, which limit sufficient development in their use.

JP-A-61-68456 describes N-aminoalkyl (meth)acrylamides, for example, N-(2-aminoethyl)acrylamide and N-(3-aminopropyl)methacrylamide, and a method for preparing the same. However, these (meth)acrylamide compounds thus obtained tend to discolor, undergo thermal polymerization or become unstable during storage with the lapse of time.

JP-A-50-89407 describes a phosphate of an aminoalkylacrylate. However, the phosphate compound is converted to a hydroxyalkyl acrylamide with the lapse of time, implying inferior storage stability.

Journal of Polymer Science: Part A: Polymer Chemistry, Vol. 46, 4984-4996 (2008) discloses a methacrylamide hydrochloride, having a primary amine structure, such as, for example, N-(2-aminoethyl)methacrylamide hydrochloride. Similar to general hydrochlorides, however, the methacrylamide hydrochloride causes corrosion of metals due to the presence of the halide ion. Moreover, an aqueous solution of the methacrylamide hydrochloride is strongly acidic and undergo thermal polymerization during storage which is problematic.

SUMMARY OF THE INVENTION

An object of the present invention is to provide a (meth)acrylamide compound that is stable during storage and has a primary amine structure containing no halide ions, and a method for preparing the compound.

As a result of intensive research, the inventors of the present invention have found that the object of the invention can be accomplished. That is, features of the invention will be described hereinafter.

1. A compound represented by the following Formula (1):

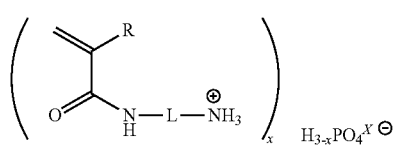

wherein R represents a hydrogen atom or a methyl group, L is a divalent linking group selected from the group consisting of —O—, a divalent aliphatic group, a divalent aromatic group and a combination thereof, and x is an integer of from 1 to 3.

2. The compound according to the above 1, wherein x in the Formula (1) is 1 or 2.
3. The compound of the above 1 or 2, wherein L in Formula (1) is a divalent linking group having from 2 to 100 carbon atoms which is a divalent aliphatic group or a combination of —O— and a divalent aliphatic group.
4. The compound according to any one of the above 1 to 3, wherein L in the Formula (1) is an ethylene group.
5. The compound of any one of the above 1 to 3, wherein L in Formula (1) is a divalent linking group represented by Formula (A):

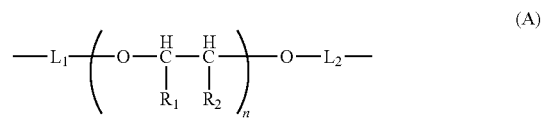

wherein each of $L_1$ and $L_2$ independently represents a alkylene group having from 1 to 3 carbon atoms, each of $R_1$ and $R_2$ independently represents a hydrogen atom or a methyl group, n is an integer from 0 to 45, and when n is an integer of 2 or more, a plurality of $R_1$ may be same or different from each other and a plurality of $R_2$ may be same or different from each other.

6. A method for preparing a compound represented by the following Formula (1), the method comprising: reacting a diamine compound represented by the following Formula (2) with a methacrylic anhydride or an acrylic anhydride under a condition where an organic acid having a pKa of 2.0 or more is present in an amount of 0.5 to 5.0 moles based on 1 mole of the diamine compound to obtain a reaction mixture; adding phosphoric acid to the reaction mixture; and purifying the reaction mixture by extraction with an organic solvent.

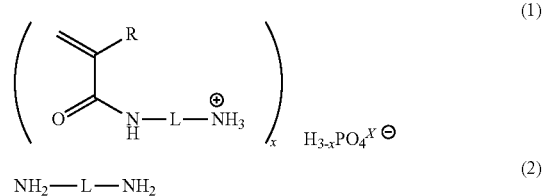

In the Formula (1), R represents a hydrogen atom or a methyl group, L is a divalent linking group selected from the group consisting of —O—, a divalent aliphatic group, a divalent aromatic group and a combination thereof, and x is an integer of from 1 to 3, and In the Formula (2), L is a divalent linking group selected from the group consisting of —O—, a divalent aliphatic group, a divalent aromatic group and a combination thereof.

The (meth)acrylamide compound according to the present invention has an improved stability during storage and has a primary amine structure containing no halide ions.

DETAILED DESCRIPTION OF THE INVENTION

The compound of the present invention is a radical polymerizable monomer represented by Formula (1):

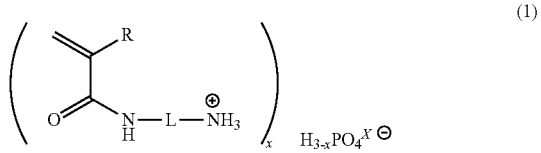

(1)

wherein R represents a hydrogen atom or a methyl group, L is a divalent linking group selected from the group consisting of —O—, a divalent aliphatic group, a divalent aromatic group and a combination thereof, and x is an integer from 1 to 3.

L in Formula (1) may be a divalent aliphatic group. Preferably, the divalent aliphatic group has a chain structure rather than a cyclic structure. Preferably, the chain is linear rather than branched. Specific examples of linear divalent aliphatic groups include alkylene groups, substituted alkylene groups, alkenylene groups, substituted alkenylene groups, alkynylene groups, substituted alkynylene groups, oxyalkylene groups and polyoxyalkylene groups. Of these, alkylene groups, substituted alkylene groups, alkenylene groups, substituted alkenylene groups, oxyalkylene groups and polyoxyalkylene groups are preferred. Alkylene groups, substituted alkylene groups, oxyalkylene groups and polyoxyalkylene groups are more preferred. Preferably, the oxyalkylene groups and polyoxyalkylene groups have the structure represented by the following Formula (A).

The number of carbon atoms in L is preferably from 2 to 100, more preferably from 2 to 30, still more preferably from 2 to 20, most preferably from 2 to 10.

Examples of substituents of the divalent aliphatic group include halogen atoms (F, Cl, Br and I), hydroxyl groups, carboxyl groups, cyano groups, aryl groups, alkoxy groups, aryloxy groups, acyl groups, alkoxycarbonyl groups, aryloxycarbonyl groups and acyloxy groups.

L in Formula (1) may be a divalent aromatic group, and the divalent aromatic group may be a substituted or unsubstituted arylene group. Specific examples of such substituted or unsubstituted arylene groups include substituted phenylene, unsubstituted phenylene, substituted naphthylene, unsubstituted naphthylene, substituted anthrylene and unsubstituted anthrylene groups. Phenylene groups are particularly preferred.

Examples of substituents of the divalent aromatic group further include alkyl groups as well as the examples mentioned as substituents of the divalent aliphatic group.

L may be a divalent linking group selected from the group consisting of —O—, a divalent aliphatic group and a combination thereof, and x is an integer from 1 to 3. The divalent linking group represented by L is preferably an alkylene group having from 1 to 8 carbon atoms or a divalent linking grout) represented by Formula (A):

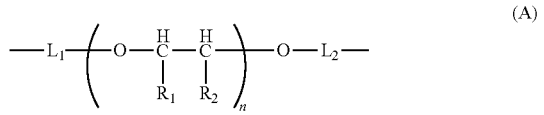

(A)

wherein each of $L_1$ and $L_2$ independently represents an alkylene group having from 1 to 3 carbon atoms, each of $R_1$ and $R_2$ independently represents a hydrogen atom or a methyl group, n is an integer from 0 to 45, and when n is an integer of 2 or more, a plurality of $R_1$ may be same or different from each other and a plurality of $R_2$ may be same or different from each other.

L in Formula (1) is a divalent linking group, and the divalent linking group is preferably an alkylene group having from 1 to 8 carbon atoms. An alkylene group having from 1 to 6 carbon atoms is preferred for ease of purchase of raw material. A linear alkylene group having from 2 to 4 carbon atoms is more preferred, and a linear alkylene group having 2 carbon atoms, i.e. an ethylene group, is most preferred.

In the divalent linking group represented by Formula (A), $L_1$ and $L_2$ are preferably same with each other for ease of purchase of raw material. It is especially preferred that $L_1$ and $L_2$ are a linear alkylene group having from 2 to 3 carbon atoms. At least one of $R_1$ and $R_2$ is preferably a hydrogen atom, and it is more preferable that both of $R_1$ and $R_2$ are a hydrogen atom. n is preferably 1 to 10, more preferably 1 or 2, and especially preferably 2.

The radical polymerizable monomer represented by Formula (1) according to the present invention may be synthesized by suitable methods described in literature and well known in the art. From the viewpoint of mass production, it is preferred to prepare the radical polymerizable monomer by the following synthetic route.

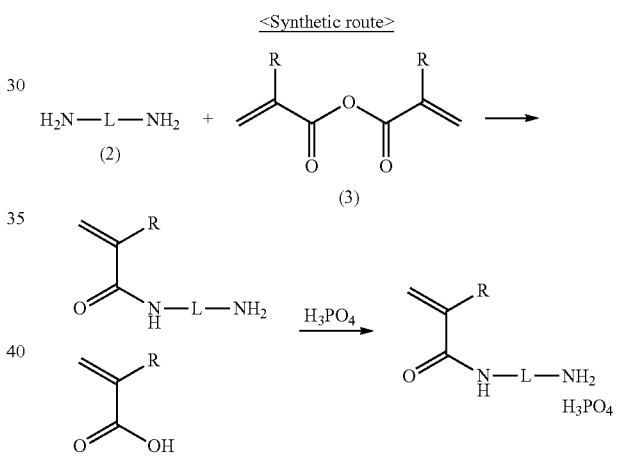

Specifically, the diamine compound represented by Formula (2) is reacted with the (meth)acrylic anhydride represented by Formula (3) preferably in water or an organic solvent mixed with water, and phosphoric acid and optionally water are added thereto. Then, the reaction mixture is purified by extraction with the organic solvent to allow impurities to migrate to the organic layer, yielding the compound represented by Formula (1).

L in Formula (2) and R in Formula (3) have the same definitions as L and R in Formula (1), respectively.

Any organic solvent may be used in the method of the present invention so long as it is inert in common reaction conditions. Examples of such solvents include tetrahydrofuran, ethylene dichloride, cyclohexane, methyl ethyl ketone, acetone, methanol, ethanol, ethylene glycol monomethyl ether, ethylene glycol monoethyl ether, 2-methoxyethyl acetate, diethylene glycol dimethyl ether, 1-methoxy-2-propanol, 1-methoxy-2-propyl acetate, N,N-dimethylformamide, N,N-dimethylacetamide, toluene, ethyl acetate, methyl lactate, ethyl lactate, dimethyl sulfoxide and water. These solvents may be used alone or as a mixture of two or more thereof.

Examples of organic solvents (extraction solvents) suitable for the extractive purification include: aliphatic hydrocarbons, such as hexane, heptane and octane; ethers, such as diethyl ether, methyl tert-butyl ether and diisopropyl ether; ketones, such as methyl n-propyl ketone, methyl n-butyl ketone and methyl isobutyl ketone; aromatic hydrocarbons, such as toluene and xylene; esters, such as methyl acetate, ethyl acetate and butyl acetate; and alcohols, such as 1-butanol, 1-pentanol, 1-hexanol, 2-butanol, 2-methyl-1-propanol, 3-methyl-1-butanol and benzyl alcohol. These organic solvents may be used alone or as a mixture of two or more thereof. The use of ethyl acetate, methyl tert-butyl ether or hexane is preferred when recovery rate and two-phase separatability are considered important.

There is no particular restriction on the amount of the extraction solvent used. The extraction solvent is preferably used in an amount ranging from 0.05 to 20-fold by mass, based on the aqueous solution including the compound represented by Formula (1).

The extractive purification may be performed once or twice or more.

The reaction may be carried out at any temperature. However, in terms of yield, the reaction temperature is preferably between $-10$ and $50°$ C., more preferably between $-10$ and $30°$ C., most preferably between $-10$ and $10°$ C.

For higher yield of the reaction, it is preferred to add an organic acid that is highly soluble in the organic solvent and has a dissociation constant lower than the first dissociation constant of phosphoric acid. That is, the organic acid is less acidic than phosphoric acid and has a pKa of 2.0 or more. The addition of the organic acid contributes to an increase in reaction selectivity and an improvement in reaction yield. The organic acid whose solubility in the organic solvent is high and acidity is lower than phosphoric acid can be easily removed after the reaction because it migrates to the organic layer during subsequent extractive purification.

The organic acid having a pKa of 2.0 or more is preferably a carboxylic acid.

Examples of suitable carboxylic acids include: $C_1$-$C_7$ aliphatic carboxylic acids (aliphatic carboxylic acids having from 1 to 7 carbon atoms), such as formic acid, acetic acid, propionic acid, methacrylic acid and butyric acid; $C_6$-$C_{10}$ aryl carboxylic acids, such as benzoic acid, 4-methylbenzoic acid, 4-methoxybenzoic acid, 4-fluorobenzoic acid, 4-chlorobenzoic acid, 2-t-butoxycarbonylaminobenzoic acid, 4-cyanobenzoic acid, 4-nitrobenzoic acid and naphthyl carboxylic acid, each of which may be unsubstituted or substituted with at least one group selected from $C_1$-$C_4$ alkyl groups, $C_1$-$C_4$ alkoxy groups (for example, methoxy, ethoxy, propoxy, isopropoxy, butoxy and isobutoxy groups, preferably methoxy and ethoxy groups, more preferably a methoxy group) and at least one halogen atom (for example, fluorine, chlorine, bromine or iodine, preferably fluorine or chlorine); and 5- to 6-membered heterocyclic carboxylic acids, such as oxazolidine-4-carboxylic acid, thiazolidine-4-carboxylic acid, 2-oxothiazolidine-4-carboxylic acid, nicotinic acid and quinolinecarboxylic acid, each of which has one to three heteroatoms selected from the group consisting of nitrogen, oxygen and sulfur atoms and may be fused with at least one phenyl ring.

From the viewpoint of solubility in the organic solvent, preferred are $C_6$-$C_{10}$ aryl carboxylic acids, such as benzoic acid, 4-methylbenzoic acid, 4-methoxybenzoic acid, 4-fluorobenzoic acid, 4-chlorobenzoic acid, 2-t-butoxycarbonylaminobenzoic acid, 4-cyanobenzoic acid, 4-nitrobenzoic acid and naphthyl carboxylic acid, each of which may be unsubstituted or substituted with at least one group selected from $C_1$-$C_4$ alkyl groups, $C_1$-$C_4$ alkoxy groups (for example, methoxy, ethoxy, propoxy, isopropoxy, butoxy and isobutoxy groups, preferably methoxy and ethoxy groups, more preferably a methoxy group) or at least one halogen atom (for example, fluorine, chlorine, bromine or iodine atom, preferably fluorine and chlorine). Benzoic acid is most preferred because of its ease of purchase.

The organic acid is preferably used in an amount ranging from 0.01 to 10.0 moles, more preferably 0.5 to 5.0 moles, most preferably 1.5 to 3.0 moles, based on one mole of the diamine compound represented by Formula (2).

Within this range, the reactivity between the diamine compound and the methacrylic anhydride or acrylic anhydride is suitably lowered and the reaction selectivity and the reaction yield are improved.

x in Formula (1) can be controlled depending on the amount of phosphoric acid added during extractive purification. Specifically, x equals to one when one equivalent of phosphoric acid is added, x equals to two when two equivalents of phosphoric acid are added, and x equals to three when three equivalents of phosphoric acid are added per equivalent of the ammonium salt in Formula (1).

For ease of purification during the extractive purification, phosphoric acid is preferably added in an amount of one or two equivalents, most preferably 1 equivalent. That is, x in Formula (1) equals preferably to one or two, most preferably one.

A radical polymerizate of the compound of Formula (1) can be synthesized by general radical polymerization methods. Radical polymerization methods that can be applied to the synthesis of the radical polymerizate are described, for example, in New Polymer Experiment 3, edited by The Society of Polymer Science, Japan and published by Kyoritsu Shuppan Co. Ltd., on Mar. 28, 1996; Synthesis and Reaction of Polymer 1, edited by The Society of Polymer Science, Japan and published by Kyoritsu Shuppan Co. Ltd., in May, 1992; New Experimental Chemistry Lecture 19, Polymer Chemistry (I), edited by The Chemical Society of Japan and published by Maruzen Bookstores Co. Ltd., on Nov. 20, 1980; and Material Engineering Lecture, Polymer Synthesis Chemistry, published by Tokyo Denki University press in September, 1995.

The radical polymerizate may be a homopolymer or a copolymer with a repeating unit other than the radical polymerizable monomer of Formula (1). Examples of monomers that are copolymerizable with the radical polymerizable monomer of Formula (1) include acrylic acid esters, methacrylic acid esters, acrylamides, methacrylamides, styrenes, acrylonitriles and methacrylonitriles.

Specific examples of the acrylic acid esters include: alkyl acrylates (each of the alkyl groups preferably has 1 to 20 carbon atoms, and more specific examples of the alkyl acrylates include methyl acrylate, ethyl acrylate, propyl acrylate, butyl acrylate, amyl acrylate, ethyl hexyl acrylate, octyl acrylate, t-octyl acrylate, chloroethyl acrylate, 2,2-dimethyl hydroxypropyl acrylate, 5-hydroxypentyl acrylate, trimethylolpropane monoacrylate, pentaerythritol monoacrylate, glycidyl acrylate, benzyl acrylate, methoxybenzyl acrylate, furfuryl acrylate, and tetrahydrofurfuryl acrylate); and aryl acrylates (for example, phenyl acrylate).

Specific examples of the methacrylic acid esters include alkyl methacrylates (each of the alkyl groups preferably has 1 to 20 carbon atoms, and more specific examples of the alkyl methacrylates include methyl methacrylate, ethyl methacrylate, propyl methacrylate, isopropyl methacrylate, amyl methacrylate, hexyl methacrylate, cyclohexyl methacrylate, benzyl methacrylate, chlorobenzyl methacrylate, octyl methacrylate, 4-hydroxybutyl methacrylate, 5-hydroxypentyl methacrylate, 2,2-dimethyl-3-hydroxypropyl methacrylate, trimethylolpropane monomethacrylate, pentaerythritol monomethacrylate, glycidyl methacrylate, furfuryl methacrylate and tetrahydrofurfuryl methacrylate); and aryl methacrylates (for example, phenyl methacrylate, cresyl methacrylate and naphthyl methacrylate).

Specific examples of the styrenes include styrene, alkylstyrenes (for example, methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene and acetoxymethylstyrene), alkoxystyrenes (for example, methoxystyrene, 4-methoxy-3-methylstyrene and dimethoxystyrene), halogenated styrenes (for example, chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene and 4-fluoro-3-trifluoromethylstyrene).

Other examples of the monomers copolymerizable with the radical polymerizable monomer of Formula (1) include acrylonitrile, methacrylonitrile, methacrylic acid, acrylic acid, and 2-acrylamido-2-methylpropane sulfonic acid.

The polymerizate obtained using the compound of the present invention preferably has a weight average molecular weight in the range of 2,000 to 1,000,000, more preferably 2,000 to 500,000, most preferably 10,000 to 500,000 in terms of handling ability.

Specific examples of compounds that can be represented by Formula (1) are described below, but the present invention is not limited thereto:

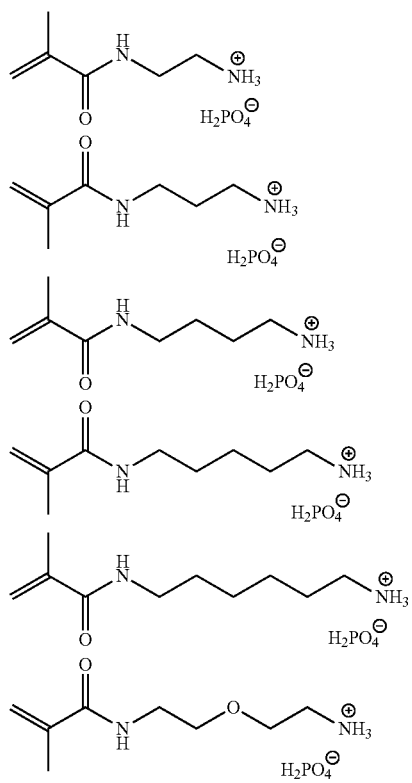

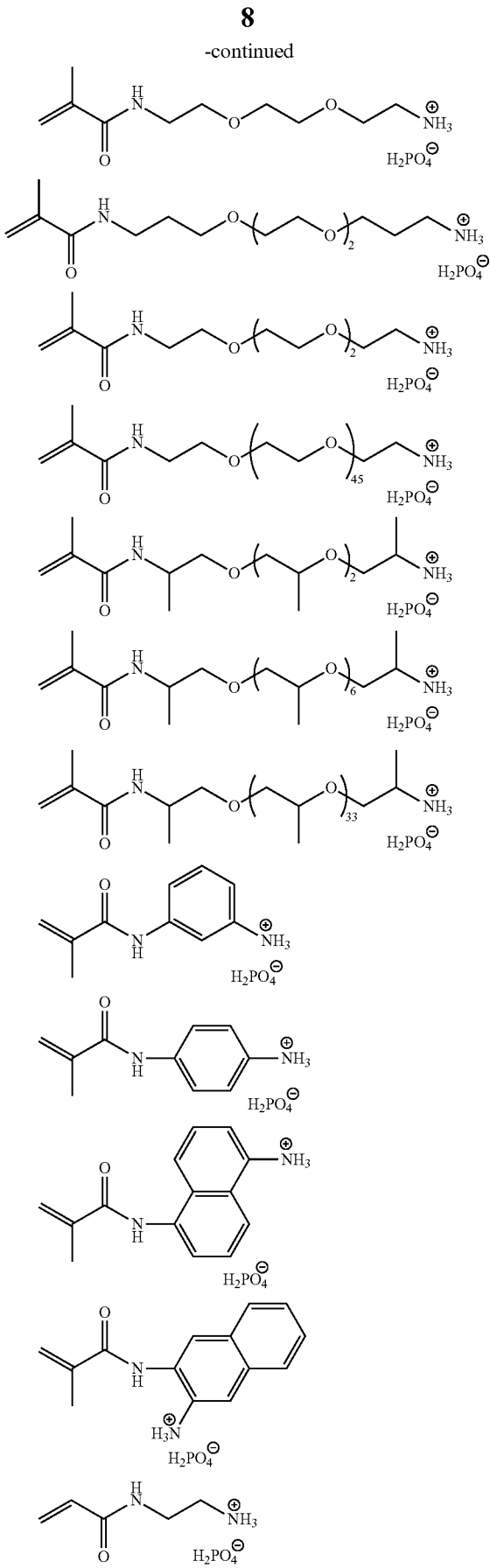

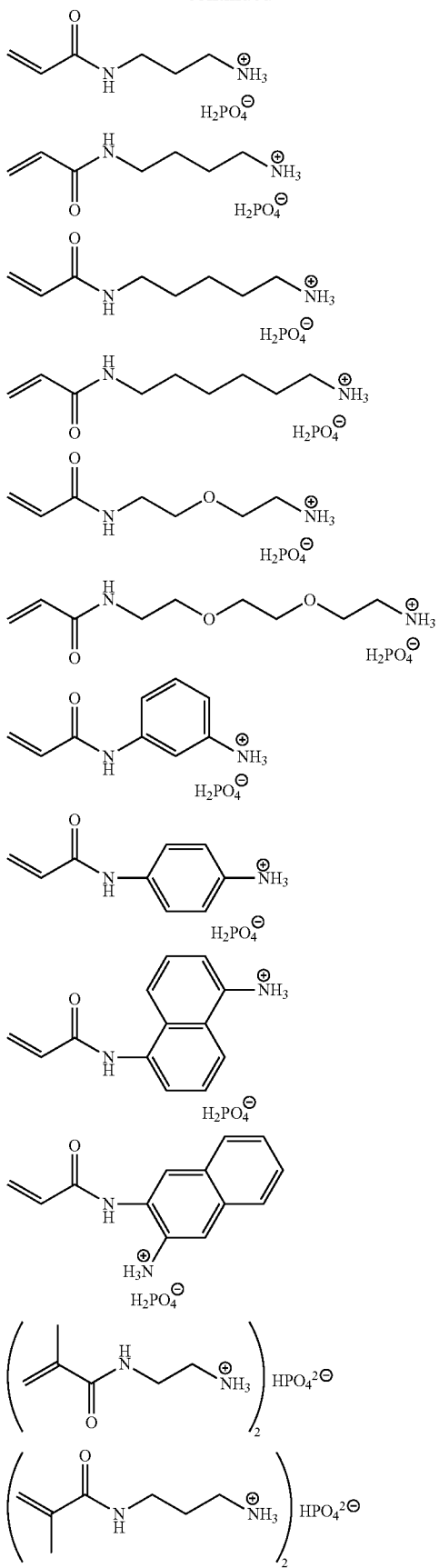
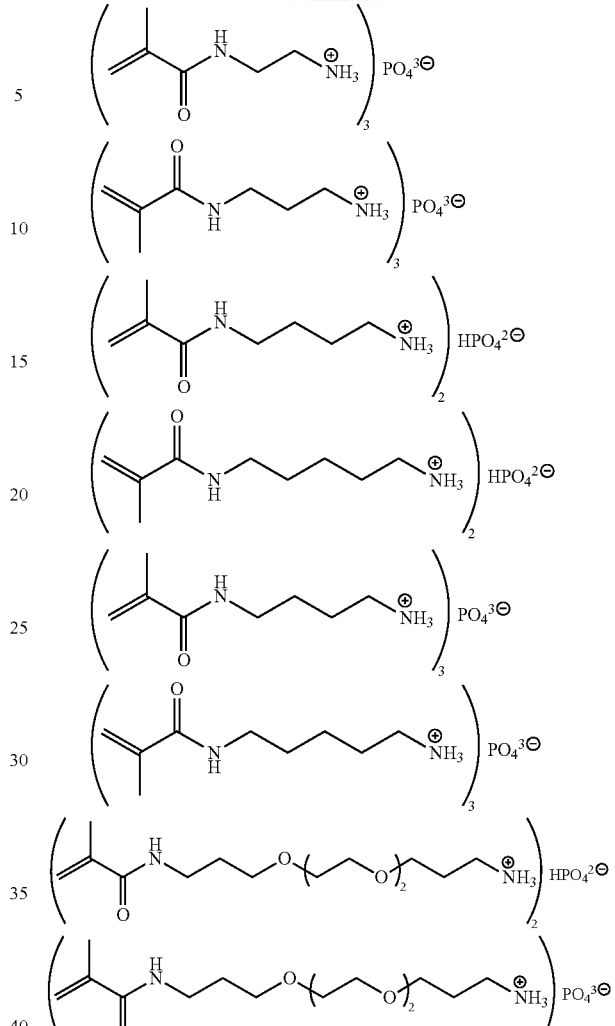

EXAMPLES

The present invention will be described in more detail with reference to the following examples. However, these examples are not intended to limit the present invention.

Synthesis Example 1

Synthesis of N-(2-aminoethyl)methacrylamide=monophosphate (M-1)

27.0 g of ethylenediamine (Wako Pure Chemical Industries, Ltd.), 225 g of ion exchanged water and 225 g of methanol were added to a three-neck flask of two liters. The internal temperature of the flask was cooled to 5° C. 114.3 g of benzoic acid (Wako Pure Chemical Industries, Ltd.) was added to the flask, and then 118.1 g of methacrylic anhydride (Sigma-Aldrich Co. LLC.) was added dropwise thereto over a period of one hour while maintaining the internal temperature at 5° C. or below. After completion of the dropwise addition, the mixture was stirred for three hours while maintaining the internal temperature at 5° C. or below. The reaction solution was allowed to rise to room temperature. The pH of the reaction solution was adjusted to 3.0 by the addition of an aqueous solution of 85 mass % phosphoric acid (Wako Pure Chemical Industries, Ltd.).

The resulting reaction solution was purified by extraction with 1,064 g of ethyl acetate and 327 g of ion exchanged water. The aqueous layer was collected, washed twice with one liter of ethyl acetate and once with one liter of hexane, followed by the addition of 13.5 mg of 4-hydroxy-2,2,6,6-tetramethylpiperidinyl-N-oxyl, affording 366.0 g of N-(2-aminoethyl)methacrylamide=monophosphate (12.5 mass % aqueous solution) (yield 45%).

The compound was identified by base titration and NMR spectroscopy.

$^1$H-NMR (400 MHz, D$_2$O): δ 5.687 (t, J=0.8 Hz, 1H), 5.422 (t, J=0.8 Hz, 1H), 3.493 (t, J=5.6 Hz, 2H), 3.099 (t, J=5.6 Hz, 2H), 1.852 (s, 3H).

Synthesis Example 2

Synthesis of N-(4-aminobutyl)methacrylamide=monophosphate (M-3)

39.67 g of butanediamine (Tokyo Chemical Industry Co. Ltd.), 225 g of ion exchanged water and 225 g of methanol were added to a three-neck flask of two liters. The internal temperature of the flask was cooled to 5° C. 114.3 g of benzoic acid (Wako Pure Chemical Industries, Ltd.) was added to the flask, and then 118.1 g of methacrylic anhydride (Sigma-Aldrich Co. LLC.) was added dropwise thereto over a period of one hour while maintaining the internal temperature at 5° C. or below. After completion of the dropwise addition, the mixture was stirred for 3 hr while maintaining the internal temperature at 5° C. or below. The reaction solution was allowed to rise to room temperature. The pH of the reaction solution was adjusted to 3.0 by the addition of an aqueous solution of 85 mass % phosphoric acid (Wako Pure Chemical Industries, Ltd.).

The resulting reaction solution was purified by extraction with 1,064 g of ethyl acetate and 327 g of ion exchanged water. The aqueous layer was collected, washed twice with one liter of ethyl acetate and once with one liter of hexane, followed by the addition of 13.5 mg of 4-hydroxy-2,2,6,6-tetramethylpiperidinyl-N-oxyl, affording 413.1 g of N-(4-aminobutyl)methacrylamide=monophosphate (13.3 mass % aqueous solution) (yield 48%).

The compound was identified by base titration and NMR spectroscopy.

$^1$H-NMR (400 MHz, D$_2$O): δ 5.58 (s, 1H), 5.33 (s, 1H), 3.20 (t, J=5.6 Hz, 2H), 2.91 (t, J=5.6 Hz, 2H), 1.82 (s, 3H), 1.60-1.5 (m, 4H).

Synthesis Example 3

Synthesis of N-(2-(2-(2-aminoethoxy)ethoxy)ethyl) methacrylamide=monophosphate (M-5)

38.9 g of 1,2-bis(2-aminoethoxy)ethane (Tokyo Chemical Industry Co. Ltd.), 112 g of ion exchanged water and 112 g of methanol were added to a three-neck flask of one liter. The internal temperature of the flask was cooled to 5° C. 59.4 g of benzoic acid (Wako Pure Chemical Industries, Ltd.) was added to the flask, and then 60.0 g of methacrylic anhydride (Sigma-Aldrich Co. LLC.) was added dropwise thereto over a period of one hour while maintaining the internal temperature at 5° C. or below. After completion of the dropwise addition, the mixture was stirred for three hours while maintaining the internal temperature at 5° C. or below. The reaction solution was allowed to rise to room temperature. The pH of the reaction solution was adjusted to 3.0 by the addition of an aqueous solution of 85 mass % phosphoric acid (Wako Pure Chemical Industries, Ltd.).

The resulting reaction solution was purified by extraction with 575 g of ethyl acetate and 178 g of ion exchanged water. The aqueous layer was collected, washed twice with one liter of ethyl acetate and once with one liter of hexane, followed by the addition of 6.7 mg of 4-hydroxy-2,2,6,6-tetramethylpiperidinyl-N-oxyl, affording 236.2 g of N-(2-(2-(2-aminoethoxy)ethoxy)ethyl)methacrylamide=monophosphate (15.0 mass % aqueous solution) (yield 43%).

The compound was identified by base titration and NMR spectroscopy.

$^1$H-NMR (400 MHz, D$_2$O): δ 5.69 (s, 1H), 5.32 (s, 1H), 3.7-3.5 (m, 8H), 3.25 (t, J=5.6 Hz, 2H), 3.19 (t, J=5.6 Hz, 2H), 1.80 (s, 3H).

Synthesis Examples 4 to 8

N-(2-aminoethyl)methacrylamide=monophosphate (M-1) was synthesized in the same manner as in Synthesis Example 1, except that the amount of benzoic acid was changed as shown in Table 1.

The yields of the compound are shown in Table 1.

TABLE 1

Relationship between the amount of the organic acid and the yield

| Synthesis Example | Amount of benzoic acid | Equivalents of benzoic acid (based on the diamine compound) | Yield |
|---|---|---|---|
| 1 | 114.3 g | 2.1 | 45% |
| 4 | 0.0 g | 0.0 | 25% |
| 5 | 27.2 g | 0.5 | 33% |
| 6 | 81.6 g | 1.5 | 41% |
| 7 | 163.2 g | 3.0 | 42% |
| 8 | 272.1 g | 5.0 | 31% |

Synthesis Example 9

Synthesis of N-(3-(2-(2-(3-aminopropoxy)ethoxy) ethoxy)propyl)methacrylamide=monophosphate (M-8)

44.1 g of diethylene glycol bis(3-aminopropyl) ether (Tokyo Chemical Industry Co. Ltd.), 96.2 g of ion exchanged water and 96.2 g of methanol were added to a three-neck flask of one liter. The internal temperature of the flask was cooled to 5° C. 48.9 g of benzoic acid (Wako Pure Chemical Industries, Ltd.) was added to the flask, and then 61.7 g of methacrylic anhydride (Sigma-Aldrich Co. LLC.) was added dropwise thereto over a period of one hour while maintaining the internal temperature at 5° C. or below. After completion of the dropwise addition, the mixture was stirred for three hours while maintaining the internal temperature at 5° C. or below. The reaction solution was allowed to rise to room temperature. The pH of the reaction solution was adjusted to 3.0 by the addition of an aqueous solution of 85 mass % phosphoric acid (Wako Pure Chemical Industries, Ltd.).

The resulting reaction solution was purified by extraction with 982 g of ethyl acetate and 144 g of ion exchanged water.

The aqueous layer was collected, washed twice with 0.4 liters of ethyl acetate and once with 0.4 liters of methyl t-butyl ether, followed by the addition of 3.9 mg of 4-hydroxy-2,2,6,6-tetramethylpiperidinyl-N-oxyl, affording 156.7 g of N-(3-(2-(2-(3-aminopropoxy)ethoxy)ethoxy)propyl)methacrylamide=monophosphate (17.8 mass % aqueous solution) (yield 36%).

The compound was identified by base titration and NMR spectroscopy.

$^1$H-NMR (400 MHz, D$_2$O): δ 5.57 (s, 1H), 5.34 (s, 1H), 3.7-3.4 (m, 12H), 3.21 (t, J=5.6 Hz, 2H), 3.01 (t, J=5.6 Hz, 2H), 1.85 (m, 5H), 1.72 (m, 2H).

The inventive compounds M-2, M-4, M-6 and M-7 were synthesized in the same manner as in the synthesis of compounds M-1, M-3, M-5 and M-8 as described in the above examples, except that the kind of the diamine component and the amount of phosphoric acid were changed.

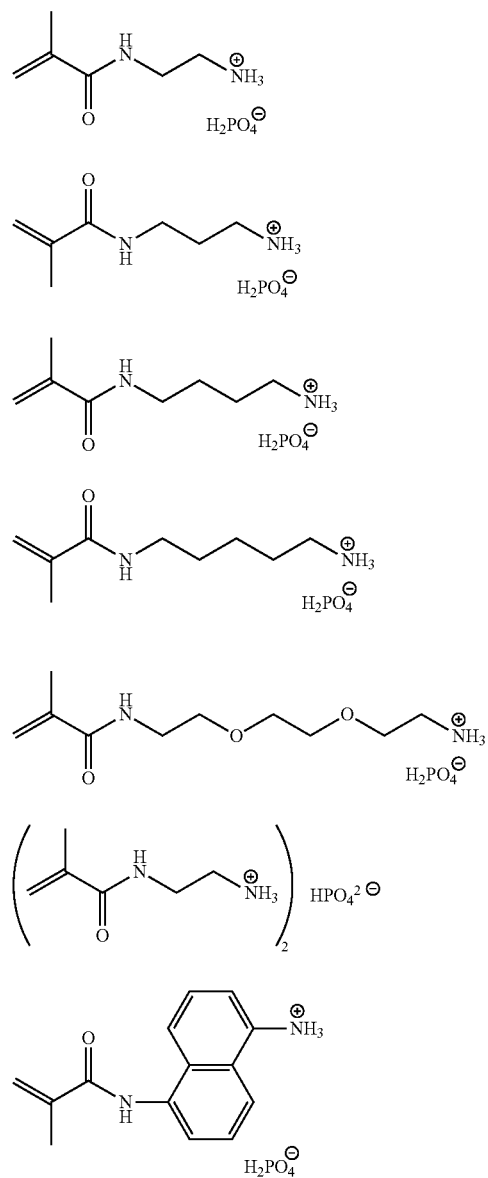

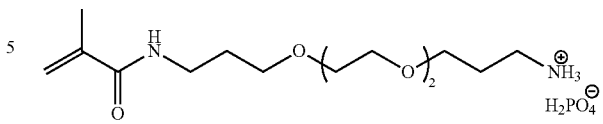

Examples 1-8 and Comparative Examples 1-5

The storage stability of the inventive compounds and the corrosion of aluminum by the inventive compounds were evaluated (Examples 1-7). Comparative compounds R-1 to R-5 were used in Comparative Examples 1-5, respectively.

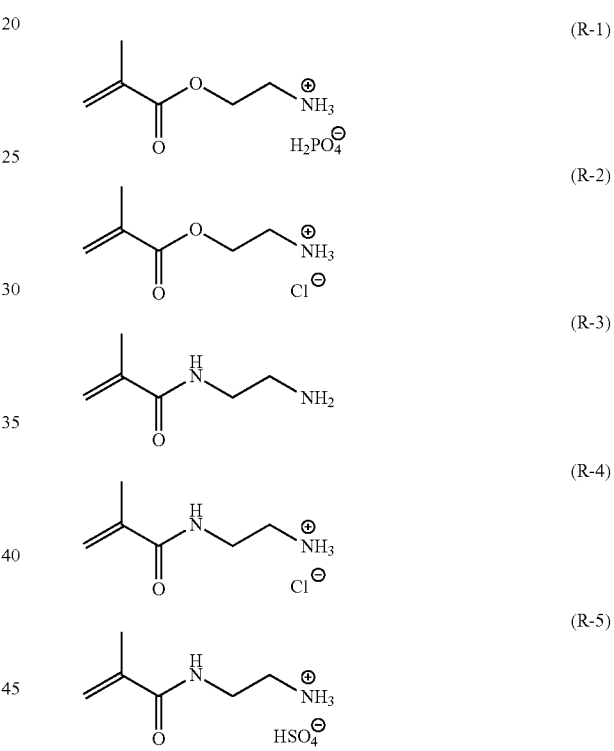

(Evaluation of Storage Stability)

An aqueous solution of each of the compounds (10 wt %) was prepared. After the aqueous solution was allowed to stand in an oven at 55° C. for 1 week, a visual observation was made as to whether a viscous polymeric material was settled.

The results are shown in Table 2. In Table 2, ○ indicates that no settling was observed and × indicates that settling was observed.

(Evaluation of Aluminum Corrosion)

An aluminum plate was dipped in an aqueous solution of each of the compounds (10 wt %). After standing at room temperature for 3 days, a visual observation was made as to whether the aluminum plate was corroded.

The results are shown in Table 2. In Table 2, ○ indicates that no corrosion was observed and × indicates that corrosion was observed.

TABLE 2

| | Evaluation results | | |
|---|---|---|---|
| | Inventive compound or comparative compound | Storage stability | Aluminum corrosion |
| Example 1 | M-1 | ○ | ○ |
| Example 2 | M-2 | ○ | ○ |
| Example 3 | M-3 | ○ | ○ |
| Example 4 | M-4 | ○ | ○ |
| Example 5 | M-5 | ○ | ○ |
| Example 6 | M-6 | ○ | ○ |
| Example 7 | M-7 | ○ | ○ |
| Example 8 | M-8 | ○ | ○ |
| Comparative Example 1 | R-1 | x | ○ |
| Comparative Example 2 | R-2 | x | x |
| Comparative Example 3 | R-3 | x | ○ |
| Comparative Example 4 | R-4 | x | x |
| Comparative Example 5 | R-5 | x | x |

The results in Table 2 reveal that the inventive compounds are very stable during storage and cause no corrosion of the metal upon contact with the metal, suggesting that the inventive compounds are useful in various applications.

The compound of the present invention can be used in various applications, including polymeric surfactants, shampoo compositions, hydrophilic members, coating materials and printing plate materials. Furthermore, the compound of the present invention can be used as an intermediate for the preparation of a polymeric compound as a component of compositions for polymeric surfactants, shampoo compositions, hydrophilic members, coating materials, printing plate materials, etc. Particularly, since the compound of the present invention and a polymeric compound prepared using the compound of the invention as an intermediate are not corrosive to metals, they are suitable for use in the production of materials using aluminum supports, for example, lithographic printing plate precursors, as described in JP-A-2009-262523.

What is claimed is:

1. A compound represented by the following Formula (1):

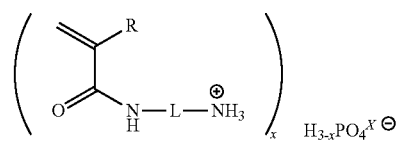

(1)

wherein R represents a hydrogen atom or a methyl group, x is an integer from 1 to 3, L is an alkylene group, an arylene group, or a divalent linking group represented by the following formula (A):

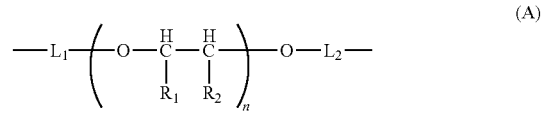

(A)

wherein each of $L_1$ and $L_2$ independently represents an alkylene group having from 1 to 3 carbon atoms, each of $R_1$ and $R_2$ independently represents a hydrogen atom or a methyl group, and n represents an integer of 0 to 45, and when n is an integer of 2 or more, a plurality of $R_1$ may be the same or different from each other and a plurality of $R_2$ may be the same or different from each other.

2. The compound according to claim 1, wherein x in the Formula (1) is 1 or 2.

3. The compound according to claim 1, wherein L in the Formula (1) is a linear alkylene group having 1 to 8 carbon atoms, a phenylene group, a naphylene group, an anthrylene group or a divalent linking group represented by the formula (A).

4. The compound according to claim 1, wherein L in the Formula (1) is a linear alkylene group having 1 to 8 carbon atoms or a divalent linking group represented by the formula (A).

5. The compound according to claim 1, wherein L in the Formula (1) is a linear alkylene group having 2 to 4 carbon atoms or a divalent linking group represented by the formula (A).

6. The compound according to claim 1, wherein L in the Formula (1) is an ethylene group or a divalent linking group represented by the formula (A).

7. The compound according to claim 1, wherein L in the Formula (1) is an ethylene group.

8. The compound according to claim 1, wherein L in the Formula (1) is a divalent linking group represented by the Formula (A).

* * * * *